United States Patent [19]

Herrnstadt et al.

[11] Patent Number: 5,002,765

[45] Date of Patent: Mar. 26, 1991

[54] **CLONING AND EXPRESSION OF *BACILLUS THURINGIENSIS* GENE TOXIC TO BEETLES OF THE ORDER COLEOPTERA**

[75] Inventors: Corinna Herrnstadt, San Diego; Edward Wilcox, Escondido, both of Calif.

[73] Assignee: Mycogen Corporation, San Diego, Calif.

[21] Appl. No.: 428,484

[22] Filed: Oct. 31, 1989

Related U.S. Application Data

[60] Continuation of Ser. No. 219,420, Jul. 15, 1988, abandoned, which is a division of Ser. No. 874,727, Jun. 16, 1986, Pat. No. 4,771,131, which is a continuation-in-part of Ser. No. 767,227, Aug. 16, 1985, abandoned.

[51] Int. Cl.$^5$ .................... A01N 63/00; C12N 15/32; C12N 15/70; C12N 15/74
[52] U.S. Cl. .................................... 424/93; 435/69.1; 435/71.2; 435/91; 435/170; 435/172.1; 435/172.3; 435/252.3; 435/252.33; 435/252.34; 435/320.1; 536/27; 935/6; 935/9; 935/22; 935/29; 935/59; 935/60; 935/61; 935/66; 935/72; 935/73
[58] Field of Search ................ 536/27; 435/69.1, 71.2, 435/91, 170.1, 172.1, 172.3, 252.3, 252.33, 252.34, 320; 424/93; 935/6, 9, 22, 29, 59, 60, 61, 66, 72, 73

[56] References Cited

U.S. PATENT DOCUMENTS

| | | | |
|---|---|---|---|
| 4,467,036 | 8/1984 | Schnepf et al. | 435/317 |
| 4,695,455 | 9/1987 | Barnes et al. | 424/93 |
| 4,771,131 | 9/1988 | Herrnstadt et al. | 536/27 |

OTHER PUBLICATIONS

Pouwells et al., 1985 Cloning Vectors, Elseviers, Amsterdam.
Klausner, A., 1984, Bio/Technology (May) 408–419.
Couch, T. L., (1980), "Mosquito Pathogenicity of *Bacillus thuringiensis* var. *Israelensis*", Developments in Industrial Microbiology 22:61–67.
Beegle, C. C., (1978), "Use of Entomogenous Bacteria in Agroecosystems", Developments in Industrial Microbiology 20:97–104.
Krieg, A., A. M. Huger, G. A. Langenbruch, and W. Schnetter (1983), "*Bacillus thuringiensis* var. tenebrionis: A New Pathotype Effective Against Coleoptera Larvae", S. ang. Ent. 96:500–508.

*Primary Examiner*—Robin L. Teskin
*Assistant Examiner*—Richard C. Peet
*Attorney, Agent, or Firm*—Saliwanchik & Saliwanchik

[57] ABSTRACT

The toxin gene encoding a protein toxic to beetles of the order Coleoptera, named M-7, has been cloned and expressed. M-7 is a novel *Bacillus thuringiensis* strain which has been deposited with a recognized culture repository. The microbe is now known as *B. thuringiensis* strain san diego.

6 Claims, No Drawings

CLONING AND EXPRESSION OF *BACILLUS THURINGIENSIS* GENE TOXIC TO BEETLES OF THE ORDER COLEOPTERA

CROSS REFERENCE TO RELATED APPLICATION

This application is a continuation of application Ser. No. 219,420, filed Jul. 15, 1988, now abandoned, which is a division of application Ser. No. 874,727, filed Jun. 16, 1986, now U.S. Pat. No. 4,771,131, which is a continuation-in-part of our copending application Ser. No. 767,227, filed on Aug. 16, 1985, now abandoned.

BACKGROUND OF THE INVENTION

The spore-forming microorganism *Bacillus thuringiensis* (Bt) produces the best-known insect toxin. The toxin is a protein, designated as δ-endotoxin. It is synthesized by the Bt sporulating cell. The toxin, upon being ingested in its crystalline form by susceptible insect larvae, is transformed into biologically active moieties by the insect gut juice proteases. The primary target is insect cells of the gut epithelium, which are rapidly destroyed. Experience has shown that the activity of the Bt toxin is so high that only nanogram amounts are required to kill susceptible insect larvae.

The reported activity spectrum of Bt covers insect species within the order Lepidoptera, which is a major insect problem in agriculture and forestry. The activity spectrum also includes the insect order Diptera, wherein reside some species of mosquitoes and blackflies. See Couch, T. L., (1980) "Mosquito Pathogenicity of *Bacillus thuringiensis* var. *israelensis*," Developments in Industrial Microbiology 22:61-67; Beegle, C. C., (1978) "Use of Entomogenous Bacteria in Agroecosystems", Developments in Industrial Microbiology, 20:97-104.

Kreig et al., Z. ang. Ent. (1983) 96:500-508, describe a Bt isolate named *Bacillus thuringiensis* var. *tenebrionis*, which is reportedly active against two beetles of the order Coleoptera. These are Colorado potato beetle, *Leptinotarsa decemlineata*, and *Agelastica alni*. This is the only known Bt isolate reported to contain such activity; all previously identified Bt strains have had activity against caterpillars (order Lepidoptera) or larvae of certain flies (order Diptera).

The Krieg et al. Bt isolate is not available for side-by-side comparison with the Bt isolate used as the source of the novel Bt gene of the subject invention. Therefore, since the Krieg et al. Bt isolate is not available to the public, the Krieg et al. publication is not a valid patent law reference under U.S. law.

BRIEF SUMMARY OF THE INVENTION

Disclosed and claimed is the cloning and expression of the toxin gene toxic to beetles of the order Coleoptera. The toxin produced by the cloned gene has activity against beetles of the order Coleoptera but not against *Trichoplusia ni*, *Spodoptera exigua* or *Aedes aegypti*. Included in the Coleoptera are various Diabrotica species (family Chrysomelidae) that are responsible for large agricultural losses. For example, *D. undecimpunctata* (western spotted cucumber beetle), *D. longicornis* (northern corn rootworm), *D. virgitera* (western corn rootworm), and *D. undecimpunctata howardi* (southern corn rootworm).

DETAILED DISCLOSURE OF THE INVENTION

The *Bacillus thuringiensis* isolate used as the source of the toxin gene of the subject invention, designated "M-7" is unusual in having a unique parasporal body (crystal) which under phase contrast microscopy is dark in appearance with a flat, square configuration.

A subculture of *B. thuringiensis* M-7, now known as *B. thuringiensis* strain *san diego* (B.t.sd) has been deposited in the permanent collection of the Northern Regional Research Laboratory, U.S. Department of Agriculture, Peoria, Ill., USA on Feb. 27, 1985. The culture was assigned the accession number NRRL B-15939 by the repository. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

*B. thuringiensis* strain *san diego*, NRRL B-15939, can be cultured using standard art media and fermentation techniques. Upon completion of the fermentation cycle, the bacteria can be harvested by first separating the Bt spores and crystals from the fermentation broth by means well known in the art. The DNA (chromosomal and plasmid) from the cells can be isolated by standard procedures and purified by procedures well known in the art. For example, such standard procedures are disclosed in Maniatis et al., Molecular Cloning (1982), Cold Spring Harbor Laboratory.

The purified DNA then can be digested with a suitable restriction endonuclease.

A gene bank of *B.t.sd* DNA then can be constructed. In the subject invention, the purified *B.t.sd* DNA, obtained as described above, was digested with the restriction endonuclease BamHI and cloned into the BamHI site of the well-known and available plasmid pBR322.

Once the gene bank of *B.t.sd* DNA was constructed, it then became necessary to construct a DNA probe to screen the gene bank. The construction of this critical DNA probe was initiated by the isolation of M-7 toxin crystals from a culture of *B.t.sd*.

The recovered M-7 toxin crystals were purified by standard procedures and then digested with trypsin to produce peptide fragments. The amino acid sequences of several of these tryptic fragments was determined by standard procedures. Subsequently, after selection of certain sequences, a probe was chemically synthesized by known means. The resulting probe was labelled and hybridized by procedures known in the art. The net result was the detection of positive clones, i.e., those that hybridized to the constructed probe.

A representative of the positive clones was subjected to a western blot using rabbit anti M-7 crystal antiserum developed by standard procedures. Confirmation of the success of the cloning and expression of M-7 toxin was obtained when a positive reaction was observed with the positive clone and the antibody against M-7 toxin crystal.

The recombinant plasmids isolated from representative positive clones were found to have a 5.8 kb DNA fragment inserted into the BamHI site. This 5.8 kb DNA fragment was excised from a representative positive clone (pCH-B3) with BamHI, purified, and then subcloned into the BamHI site of the known and available plasmid pRO1614 (J. Bact. [1982]150:60; U.S. Pat. No. 4,374,200). Plasmid pRO1614 is available from the Northern Regional Research Laboratory, address below, where its deposit number is NRRL B-12127. The plasmid is derived from pBR322 and has unique HindIII, BamHI, and SalI and PvuII restriction sites; a PstI insertion includes the carbenicillin resistance gene and a *P. aeruginosa* replication system. *Pseudomonas fluorescens* was transformed with this constructed shuttle vector and the expression of M-7 toxin was verified by its identification of a western blot.

Plasmid pCH-B3, or plasmid pRO1614 with the 5.8 kb fragment insert, can be recovered from their bacterial hosts by well-known procedures, e.g., using the cleared lysate-isopycnic density gradient procedures. If desired, the 5.8 kb fragment can be excised from pRO1614 by digestion with BamHI and cloned into a different vector for transformation into another host. These procedures are all well known to persons skilled in the art.

Plasmid pCH-B3, in an *E. coli* host, was deposited with the ARS Patent Collection, Culture Collection Research-Fermentation Laboratory, Norther Regional Research Center Peoria, Ill. 61604. The deposit was made in the permanent collection of the repository to be maintained by the repository for at least 30 years. The deposit was made on July 18, 1985, and given the accession number NRRL B-15981. A subculture is available to the public upon the grant of a patent disclosing the deposit. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

The toxin gene of the subject invention can be introduced into a wide variety of microbial hosts. Expression of the toxin gene (M-7) results, directly or indirectly, in the interacellular production and maintenance of the pesticide. With suitable hosts, e.g., *Pseudomonas*, the microbes can be applied to the situs of beetles of the order Coleoptera where they will proliferate and be ingested by the susceptible beetles. The result is a control of the unwanted beetles. Alternatively, the microbe hosting the toxin M-7 gene can be treated under conditions that prolong the activity of the toxin produced in the cell. The treated cell then can be applied to the environment of target pest(s). The resulting product retains the toxicity of the M-7 toxin.

Where the M-7 toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of plant leaves) and/or the rhizosphere (the soil surrounding plant roots) of a wide variety of important crops. These microorganisms include bacteria, algae, and fungi. Of particular interest are microorganism, such as bacteria, e.g., genera *Pseudomonas, Erwinia, Serratia, Xanthomonas, Streptomyces, Rhizobium, Rhodopseudomonas, Agrobacterium, Acetobacter, Lactobacillus, Arthrobacter, Azotobacter, Leuconostoc,* and *Alcaligenes;* fungi, particularly yeast, e.g., genera *Saccharomyces, Cryptococcus, Kluyveromyces, Sporobolomyces, Rhodotorula,* and *Aureobasidium.* Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae* and *Aureobasidium pollulans.* Of particular interest are the pigmented microorganisms.

A wide variety of ways are available for introducing the M-7 gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will occur only after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In a direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop condon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct or may be combined as a separate DNA fragment with the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototrophy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the filed. For example, genes expressing metal chelating agents, e.g., siderophores, may be introduced into the host along with the structural gene expressing the toxin. In this manner, the enhanced expression of a sideophore may provide for a competitive advantage for the toxin producing host, so that it may effectively compete with the wild-type microorganisms and stably occupy a niche in the environment of the vegetation to be protected.

Where no functional replication system is present, the construct will also include a sequence of at least 50 bp, preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that the toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898; 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270; 4,362,817; and 4,371,625.

The M-7 gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Preferred hosts, particularly those in the phytosphere, will have certain characteristics which enhance the environmental stability of the toxins in the host. Protective qualities include a low level of proteolytic degradation, thick cell walls, pigmentation, and the like. Other characteristics of interest for the host include leaf affinity, lack of mammalian toxicity, attractiveness to pests for ingestion, ease of handling and storage, rate of proliferation in the field, competitiveness, and the like.

In the field applications, the transformant strain will be applied to its natural habitat, such as the rhizosphere or phylloplane of the plant to be protected from the pest. The transformant strain will grow in its natural habitat, while producing the M-7 toxin which will be absorbed and/or ingested by the larvae or adult pest, or have a toxic effect on the ova. The persistence of the microorganisms will provide for long-term protection of the vegetation, although repetitive administrations may be required from time to time. The organism may be applied by spraying, soaking injection into the soil, seed coating, seedling coating or spraying, or the like. Where administered in the field, generally concentrations of the organism will be from $10^6$ to $10^{10}$ cells/ml, and the volume applied per hectare will be generally from about 0.1 to 2 lbs or more. Where administered to a plant part, the concentration of the organism will usually be from $10^3$ to $10^6$ cells/cm$^2$.

Suitable host cells, where the pesticide-containing cells will be treated to prolong the activity of the toxin in the cell when the then dead cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and lower eukaryotes, such as fungi. Illustrative prokaryotes, both Gram-negative and -positive, include Enterobacteriaceae, such as *Escherichia, Erwinia, Shigella, Salmonella,* and *Proteus;* Bacillaceae; Rhizobiaceae, such as *Rhizobium;* Spirillaceae, such as photobacterium, *Zymomonas, Serratia, Aeromonas, Vibrio, Desulfovibrio, Spirillum;* Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the M-7 gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include east of formulation and handling, economics, storage stability, and the like.

Host organisms of particular interest include yeast, such as Rhodotorula sp., Aureobasidium sp., Saccharomyces sp., and Sporobolomyces sp., phylloplane organisms such as Pseudomonas sp., Erwinia sp. and Flavobacterium sp.; or such other organisms as Escherichia, Lactobacillus sp., Bacillus sp., and the like. Specific organisms include Pseudomonas aeruginosa, Pseudomonas fluorescens, Saccharomyces cerevisiae, Bacillus thuringiensis, Escherichia coli, Bacillus subtilus, and the like.

The cell will usually be intact and be substantially in the proliferative form when killed, rather than in a spore form, although in some instances spores may be employed.

The cells may be inhibited from proliferation in a variety of ways, so long as the technique does not deleteriously affect the properties of the pesticide, nor diminish the cellular capability in protecting the pesticide. The techniques may involve physical treatment, chemical treatment, changing the physical character of the cell or leaving the physical character of the cell substantially intact, or the like.

Various techniques for inactivating the host cells include heat, usually 50° C. to 70° C.; freezing; UV irradiation; lyophilization; toxins, e.g., antibiotics; phenols; anilides, e.g., carbanilide and salicylanilide; hydroxyurea; quaternaries; alcohols; antibacterial dyes; EDTA and amidines; non-specific organic and inorganic chemicals, such as halogenating agents, e.g., chlorinating, brominating or iodinating agents; aldehydes, e.g., glutaraldehyde or formaldehyde; toxic gases, such as ozone and ethylene oxide; peroxide; psoralens; desiccating agents or the like, which may be used individually or in combination. The choice of agent will depend upon the particular pesticide, the nature of the host cell, the nature of the modification of the cellular structure, such as fixing and preserving the cell wall with cross-linking agents, or the like.

The cells generally will have enhanced structural stability which will enhance resistance to environmental degradation in the field. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The cellular host containing the M-7 pesticidal gene may be grown in any convenient nutrient medium, where the DNA construct provides a selective advantage, providing for a selective medium so that substantially all or all of the cells retain the M-7 gene. These cells may then be harvested in accordance with conventional ways. Alternatively, the cells can be fixed prior to harvesting.

The method of treating the host organism containing the toxin can fulfill a number of functions. First, it may enhance structural integrity. Second, it may provide for enhanced proteolytic stability of the toxin, by modifying the toxin so as to reduce its susceptibility to proteolytic degradation and/or by reducing the proteolytic activity of proteases naturally present in the cell. The cells are preferably modified at an intact stage and when there has been a substantial buildup of the toxin protein. These modifications can be achieved in a variety of ways, such as by using chemical reagents having a broad spectrum of chemical reactivity. The intact cells can be combined with a liquid reagent medium containing the chemical reagents, with or without agitation, at temperatures in the range of about $-10°$ to $60°$ C. The reaction time may be determined empirically and will vary widely with the reagents and reaction conditions. Cell concentrations will vary from about $10^2$ to $10^{10}$ per ml.

Of particular interest as chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (see Humason, Gretchen L., Animal Tissue Techniques, W. H. Freeman and Company, 1967); or a combination of physical (heat) and chemical agents that prolong the activity of the toxin produced in the cell when the cell is applied to the environment of the target pest(s).

For halogenation with iodine, temperatures will generally range from about 0° to 50° C., but the reaction can be conveniently carried out at room temperature. Conveniently, the iodination may be performed using triiodide or iodine at 0.5 to 5% in an acidic aqueous medium, particularly an aqueous carboxylic acid solution that may vary from about 0.5–5M. Conveniently, acetic acid may be used, although other carboxylic acids, generally of from about 1 to 4 carbon atoms, may also be employed. The time for the reaction will generally range from less than a minute to about 24 hr, usually from about 1 to 6 hr. Any residual iodine may be removed by reaction with a reducing agent, such as dithionite, sodium thiosulfate, or other reducing agent compatible with ultimate usage in the field. In addition, the modified cells may be subjected to further treatment, such as washing to remove all of the reaction medium, isolation in dry form, and formulation with typical stickers, spreaders, and adjuvants generally utilized in agricultural applications, as is well known to those skilled in the art.

Of particular interest are reagents capable of cross-linking the cell wall. A number of reagents are known in the art for this purpose. The treatment should result in enhanced stability of the pesticide. That is, there should be enhanced persistence or residual activity of the pesticide under field conditions. Thus, under conditions where the pesticidal activity of untreated cells diminishes, the activity of treated cells remains for periods of from 1 to 3 times longer.

The cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest(s), e.g., plants, soil or water, by spraying, dusting, sprinkling or the like.

Following are examples which illustrate procedures, including the best mode, for practicing the invention. These examples should not be construed as limiting. All percentages are by weight and all solvent mixture proportions are by volume unless otherwise noted.

EXAMPLE 1—Culturing B. thuringiensis strain san diego NRRL B-15939.

A subculture or starter culture of B. thuringiensis strain san diego NRRL B-15939 can be used to inoculate the following medium, known as LB broth:

| | | |
|---|---|---|
| Tryptone | 10 | gm |
| Yeast extract | 5 | gm |
| NaCl | 5 | gm |
| 5N NaOH | 0.6 | ml |
| Water | 1000 | ml |

As per standard microbiological techniques, the above medium would be sterilized prior to inoculation and the inoculations would be done using aseptic procedures. The M-7 cells are grown for 3-4 days at 30° C.

A detailed procedure is as follows:

A series of 150 ml Erlenmeyer flasks containing sterile PWYE medium (peptone 5.0%; yeast extract 0.1%; NaCl 0.5% in 1 liter of water; adjust pH to 7.5) are inoculated from a petri plate culture of B. thuringiensis strain san diego, NRRL B-15939. The flasks are incubated at 30° C. on a rotary shaker (200 rpm) overnight. From this starter culture, 300 ml of LB broth in a 2-liter flask is inoculated using 7.5 ml of the starter. The LB-broth flasks are incubated under the same conditions as the starter, but are harvested after 4 days.

The above procedure can be readily scaled up to large fermentors by procedures well known in the art.

The Bt spores and crystals, obtained in the above fermentation, can be isolated by procedures well known in the art. A frequently-used procedure is to subject the harvested fermentation broth to separation techniques, e.g., centrifugation.

EXAMPLE 2—Cloning and Expression of M-7 Toxin Gene

Total DNA (chromosomal and plasmid) was isolated from the M-7 cells of Example 1 and purified by standard procedures. The resulting purified DNA was digested with the restriction endonuclease BamHI, using the supplier's instruction. The digested DNA was then cloned into the BamHI site of the well-known plasmid pBR322 to give a gene bank of M-7 DNA. This cloning procedure was done following standard well-known procedures.

A DNA probe to screen the gene bank was obtained as follows: M-7 crystals were isolated from a culture grown in NYSM medium (10 gm tryptone, 5 gm NaCl, 55 gm yeast extract, 2 gm $MgSO_4.7H_2O$, 1000 ml water, pH 7.5) overnight at 30° C. The purified crystals were dissolved in 8 urea, 0.1 M glycine, pH 8.2 and digested with trypsin overnight at room temperature. The resulting peptide fragments were separated on a $C_4$ reverse phase high pore column with a 180 min gradient of 91% solution A (0.1% trifluoroacetic acid in $H_2O$) to 40% solution A in 0.1% trifluoroacetic acid in acetonitrile. The aminoacid sequences of several tryptic fragments were obtained and a sequence of 6 aminoacids were selected for synthesis of a mixed probe, 17 bases in length, with a redundancy of 32.

The probe was end-labeled with polynucleotide kinase and [$\gamma$-$^{32}$P]ATP and hybridized to bacterial colonies containing recombinant plasmids as constructed for the M-7 gene bank. The colony filters were prepared according to Hanahan and Meselson (1980) Gene 10:63–67. Positive colonies were identified by autoradiography. The recombinant plasmids isolated from seven positive clones (pCH-B3 as representative) were found to have a 5.8 kb (kilobase pairs) DNA fragment inserted into the BamHI site.

A western blot (Burnette, W. N. [1981] Anal. Biochem. 112:195) of pCH-B3 was performed on an SDS-PAGE of an overnight culture, using rabbit anti-M-7 crystal antiserum. A protein of about 86 kilodalton was identified. The clone pCH-B3, therefore, contains an M-7 DNA fragment that encodes for a protein having serological identity with the protein from the M-7 crystals. The recombinant protein may be bigger than the toxin from solubilized M-7 crystals because of unavailability of transcriptional and/or translational stop signals in the given plasmid construction.

The nucleotide sequence encoding the B.t.sd toxin gene is shown in Table A. The deduced amino acid sequence is shown in Table B.

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence corresponds to the mRNA sequence, with thymine substituted for uracil. The letters stand for the purine or pyrimidine bases forming the deoxynucleotide sequence.

A = adenine
G — guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T is W is C
Z = A or G if W is A
QR = TC if S is A, G, C or T; alternatively QR = AG if S is T or C
J = A or G
K = T or C
L = A, T, C or G
M — A, C or T The above shows that the novel amino acid sequence of the M7 toxin, and other useful proteins, can be prepared by equivalent nucleotide sequences encoding the same amino acid sequence of the proteins. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J., [1984] Science 223:249–255). Thus, the subject invention includes mutants of the amino acid sequence depicted herein which do not alter the protein secondary structure, or if the structure is altered, the biological activity is retained to some degree.

EXAMPLE 3—Production of M-7 Toxin Protein by Clone pCH-B3

A 20 liter culture of pCH-B3 (L-broth with 70 μg/ml Ampicillin) was grown in a fermenter and harvested at OD600=3.35. The cell pellet was washed with water and resuspended in 500 ml glycine buffer (0.1 M glycine, pH 8.0 with tris base) containing 2 g lysozyme, 1 mM PMSF (phenylmethylsulfonyl fluoride), 1 mM TPCK (1-tosylamide-2-phenyl ethylchloromethyl ketone), and 500 μg DNase I and incubated at room temperature for 30 min. The pH was then raised to 10 with NaOH and the cells were further ruptured in a bead beater (Biospec Products, Bartlesville, Okla.) on ice with four 30 second bursts 5 min apart. The extract was then centrifuged at 10,000×g for 30 min.

EXAMPLE 4—Isolation and Purification of M-7 Toxin Protein Produced by Clone pCH-B3

The protein from pCH-B3 was purified using affinity chromatography (Cuatrecasa, P. and Anfinsen, C. B. [1971] Meth. Enzymology Vol. 22 [ed. W. B. Jacoby] Acad. Press, N.Y.) as follows: Sepharose was activated with cyanogen bromide as described by Cuatrecasa and Anfinsen. Rabbit anti-M-7 crystal serum was added to the activated Sepharose and incubated overnight at room temperature with constant agitation. The affinity resign was then washed with 1% ethanolamine, 3 M NaCl, pH 9.2, and then with TBS (0.02 M tris-HCl, 0.07 M NaCl, pH 7.5) containing 0.02% sodium azide. The column was equilibrated in 0.1 M glycine pH 10 (with tris base) containing 1 mM EDTA (ethylenediaminetetraacetic acid), 1 mM PMSF, 1 mM TPCK, and 0.02% sodium azide. The E. coli extract, prepared above, was loaded onto the column and recirculated for 64 hr at 4° C. The extract was washed from the column with 1 M NaCl and 0.1 M glycine-tris pH 10, and the bound M-7 toxin was removed from the column with 3 M sodium perchlorate, 0.1 M glycine-tris pH 10. The M-7 toxin was then dialyzed against water and concentrated (MicroPro D: Con, Pierce Chem. Co., Rockford, Ill.).

The purified M-7 toxin can be administered (applied) to vegetation susceptible to infestation by beetles of the order Coleoptera to protect the vegetation. Advantageously, the M-7 toxin will be made environmentally by use of suitable coatings well known to persons skilled in the art.

EXAMPLE 5—Subcloning and Expression of M-7 Toxin Gene into *Pseudomonas fluorescens*

The 5.8 kb DNA fragment carrying the M-7 toxin gene was excised from plasmid pCH-B3 with BamHI, purified, and subcloned into the BamHI site of the plasmid pRO1614. *Pseudomonas fluorescens* was transformed with this plasmid. The expression of M-7 toxin by recombinant Pseudomonas cells was verified by its identification on a western blot.

EXAMPLE 6—Testing of *B. thuringiensis* strain san diego NRRL B-15939 Spores and Crystal

*B. thuringiensis* strain san diego NRRL B-15939 spores and crystal, obtained as described above, were tested against various insects. The insect species tested and a summary of the results are listed in Table 1.

The method used to test for *D. undecimpunctata* (WSCB) activity consisted of spraying a spore/crystal suspension onto leaf discs of lettuce in a spray tower apparatus. (The larvae of this species are reared on lettuce leaves.) The spray was dried in a laminar flow hood and placed in a container on moist filter paper. Ten larvae of WSCB were added and the containers were incubated at 25° C. and 14 hr photoperiod. Fresh treated discs were added as needed. Inhibition of feeding was noted and mortality was recorded at 5 and 7 days. Results of 2 bioassays are given in Table 2.

In order to test the M-7 toxin for activity against *Pyrrhalta luteola* (elm leaf beetle), a suspension of solubilized protein from M-7 crystals was applied to elm leaves. The dried leaves were then placed in a container on moist sand. Five to ten larvae of P. luteola were added and the containers were incubated at room temperature. Mortality was recorded at 3 and 5 days. An $LC_{50}$ of 120 ng toxin/cm² of leaf surface was calculated from these arrays.

TABLE A

**Nucleotide Sequence Encoding the *Bacillus thuringiensis* strain *san diego* Toxin Gene**

| | | | | |
|---|---|---|---|---|
| | | | ATGA | ATCCGAACAA |
| TCGAAGTGAA | CATGATACAA | TAAAAACTAC | TGAAAATAAT | GAGGTGCCAA |
| CTAACCATGT | TCAATATCCT | TTAGCGGAAA | CTCCAAATCC | AACACTAGAA |
| GATTTAAATT | ATAAAGAGTT | TTTAAGAATG | ACTGCAGATA | ATAATACGGA |
| AGCACTAGAT | AGCTCTACAA | CAAAAGATGT | CATTCAAAAA | GGCATTTCCG |
| TAGTAGGTGA | TCTCCTAGGC | GTAGTAGGTT | TCCCGTTTGG | TGGAGCGCTT |
| GTTTCGTTTT | ATACAAACTT | TTTAAATACT | ATTTGGCCAA | GTGAAGACCC |
| GTGGAAGGCT | TTTATGGAAC | AAGTAGAAGC | ATTGATGGAT | CAGAAAATAG |
| CTGATTATGC | AAAAAATAAA | GCTCTTGCAG | AGTTACAGGG | CCTTCAAAAT |
| AATGTCGAAG | ATTATGTGAG | TGCATTGAGT | TCATGGCAAA | AAAATCCTGT |
| GAGTTCACGA | AATCCACATA | GCCAGGGGCG | GATAAGAGAG | CTGTTTTCTC |
| AAGCAGAAAG | TCATTTTCGT | AATTCAATGC | CTTCGTTTGC | AATTTCTGGA |
| TACGAGGTTC | TATTTCTAAC | AACATATGCA | CAAGCTGCCA | ACACACATTT |
| ATTTTTACTA | AAAGACGCTC | AAATTTATGG | AGAAGAATGG | GGATACGAAA |
| AAGAAGATAT | TGCTGAATTT | TATAAAAGAC | AACTAAAACT | TACGCAAGAA |
| TATACTGACC | ATTGTGTCAA | ATGGTATAAT | GTTGGATTAG | ATAAATTAAG |
| AGGTTCATCT | TATGAATCTT | GGGTAAACTT | TAACCGTTAT | CGCAGAGAGA |
| TGACATTAAC | AGTATTAGAT | TTAATTGCAC | TATTTCCATT | GTATGATGTT |
| CGGCTATACC | CAAAAGAAGT | TAAAACCGAA | TTAACAAGAG | ACGTTTTAAC |
| AGATCCAATT | GTCGGAGTCA | ACAACCTTAG | GGGCTATGGA | ACAACCTTCT |
| CTAATATAGA | AAATTATATT | CGAAAACCAC | ATCTATTTGA | CTATCTGCAT |
| AGAATTCAAT | TTCACACGCG | GTTCCAACCA | GGATATTATG | GAAATGACTC |
| TTTCAATTAT | TGGTCCGGTA | ATTATGTTTC | AACTAGACCA | AGCATAGGAT |
| CAAATGATAT | AATCACATCT | CCATTCTATG | GAAATAAATC | CAGTGAACCT |
| GTACAAAATT | TAGAATTTAA | TGGAGAAAAA | GTCTATAGAG | CCGTAGCAAA |
| TACAAATCTT | GCGGTCTGGC | CGTCCGCTGT | ATATTCAGGT | GTTACAAAAG |
| TGGAATTTAG | CCAATATAAT | GATCAAACAG | ATGAAGCAAG | TACACAAACG |
| TACGACTCAA | AAAGAAATGT | TGGCGCGGTC | AGCTGGGATT | CTATCGATCA |
| ATTGCCTCCA | GAAACAACAG | ATGAACCTCT | AGAAAAGGGA | TATAGCCATC |
| AACTCAATTA | TGTAATGTGC | TTTTTAATGC | AGGGTAGTAG | AGGAACAATC |
| CCAGTGTTAA | CTTGGACACA | TAAAAGTGTA | GACTTTTTTA | ACATGATTGA |
| TTCGAAAAAA | ATTACACAAC | TTCCGTTAGT | AAAGGCATAT | AAGTTACAAT |
| CTGGTGCTTC | CGTTGTCGCA | GGTCCTAGGT | TTACAGGAGG | AGATATCATT |
| CAATGCACAG | AAAATGGAAG | TGCGGCAACT | ATTTACGTTA | CACCGGATGT |
| GTCGTACTCT | CAAAAATATC | GAGCTAGAAT | TCATTATGCT | TCTACATCTC |
| AGATAACATT | TACACTCAGT | TTAGACGGGG | CACCATTTAA | TCAATACTAT |
| TTCGATAAAA | CGATAAATAA | AGGAGACACA | TTAACGTATA | ATTCATTTAA |
| TTTAGCAAGT | TTCAGCACAC | CATTCGAATT | ATCAGGGAAT | AACTTACAAA |
| TAGGCGTCAC | AGGATTAAGT | GCTGGAGATA | AAGTTTATAT | AGACAAAATT |
| GAATTTATTC | CAGTGAAT | | | |

TABLE B

**Deduced Amino Acid Sequence of *Bacillus thuringiensis* strain san diego Toxin**

| | | | | 5 | | | | | 10 | | | | | 15 | | | | | 20 |
|---|---|---|---|---|---|---|---|---|---|---|---|---|---|---|---|---|---|---|---|
| Met | Asn | Pro | Asn | Asn | Arg | Ser | Glu | His | Asp | Thr | Ile | Lys | Thr | Thr | Glu | Asn | Asn | Glu | Val |
| | | | | 25 | | | | | 30 | | | | | 35 | | | | | 40 |
| Pro | Thr | Asn | His | Val | Gln | Tyr | Pro | Leu | Ala | Glu | Thr | Pro | Asn | Pro | Thr | Leu | Glu | Asp | Leu |
| | | | | 45 | | | | | 50 | | | | | 55 | | | | | 60 |
| Asn | Tyr | Lys | Glu | Phe | Leu | Arg | Met | Thr | Ala | Asp | Asn | Asn | Thr | Glu | Ala | Leu | Asp | Ser | Ser |
| | | | | 65 | | | | | 70 | | | | | 75 | | | | | 80 |
| Thr | Thr | Lys | Asp | Val | Ile | Gln | Lys | Gly | Ile | Ser | Val | Val | Gly | Asp | Leu | Leu | Gly | Val | Val |
| | | | | 85 | | | | | 90 | | | | | 95 | | | | | 100 |
| Gly | Phe | Pro | Phe | Gly | Gly | Ala | Leu | Val | Ser | Phe | Tyr | Thr | Asn | Phe | Leu | Asn | Thr | Ile | Trp |
| | | | | 105 | | | | | 110 | | | | | 115 | | | | | 120 |
| Pro | Ser | Glu | Asp | Pro | Trp | Lys | Ala | Phe | Met | Glu | Gln | Val | Glu | Ala | Leu | Met | Asp | Gln | Lys |
| | | | | 125 | | | | | 130 | | | | | 135 | | | | | 140 |
| Ile | Ala | Asp | Tyr | Ala | Lys | Asn | Lys | Ala | Leu | Ala | Glu | Leu | Gln | Gly | Leu | Gln | Asn | Asn | Val |
| | | | | 145 | | | | | 150 | | | | | 155 | | | | | 160 |
| Glu | Asp | Tyr | Val | Ser | Ala | Leu | Ser | Ser | Trp | Gln | Lys | Asn | Pro | Val | Ser | Ser | Arg | Asn | Pro |
| | | | | 165 | | | | | 170 | | | | | 175 | | | | | 180 |
| His | Ser | Gln | Gly | Arg | Ile | Arg | Glu | Leu | Phe | Ser | Gln | Ala | Glu | Ser | His | Phe | Arg | Asn | Ser |
| | | | | 185 | | | | | 190 | | | | | 195 | | | | | 200 |
| Met | Pro | Ser | Phe | Ala | Ile | Ser | Gly | Tyr | Glu | Val | Leu | Phe | Leu | Thr | Thr | Tyr | Ala | Gln | Ala |
| | | | | 205 | | | | | 210 | | | | | 215 | | | | | 220 |
| Ala | Asn | Thr | His | Leu | Phe | Leu | Leu | Lys | Asp | Ala | Gln | Ile | Tyr | Gly | Glu | Glu | Trp | Gly | Tyr |
| | | | | 225 | | | | | 230 | | | | | 235 | | | | | 240 |
| Glu | Lys | Glu | Asp | Ile | Ala | Glu | Phe | Tyr | Lys | Arg | Gln | Leu | Lys | Leu | Thr | Gln | Glu | Tyr | Thr |
| | | | | 245 | | | | | 250 | | | | | 255 | | | | | 260 |
| Asp | His | Cys | Val | Lys | Trp | Tyr | Asn | Val | Gly | Leu | Asp | Lys | Leu | Arg | Gly | Ser | Ser | Tyr | Glu |
| | | | | 265 | | | | | 270 | | | | | 275 | | | | | 280 |
| Ser | Trp | Val | Asn | Phe | Asn | Arg | Tyr | Arg | Arg | Glu | Met | Thr | Leu | Thr | Val | Leu | Asp | Leu | Ile |
| | | | | 285 | | | | | 290 | | | | | 295 | | | | | 300 |
| Ala | Leu | Phe | Pro | Leu | Tyr | Asp | Val | Arg | Leu | Tyr | Pro | Lys | Glu | Val | Lys | Thr | Glu | Leu | Thr |
| | | | | 305 | | | | | 310 | | | | | 315 | | | | | 320 |
| Arg | Asp | Val | Leu | Thr | Asp | Pro | Ile | Val | Gly | Val | Asn | Asn | Leu | Arg | Gly | Tyr | Gly | Thr | Thr |

TABLE B-continued

Deduced Amino Acid Sequence of *Bacillus thuringiensis* strain san diego Toxin

```
                              325                          330                          335                          340
Phe  Ser  Asn  Ile  Glu   Asn  Tyr  Ile  Arg  Lys   Pro  His  Leu  Phe  Asp   Tyr  Leu  His  Arg  Ile
                              345                          350                          355                          360
Gln  Phe  His  Thr  Arg   Phe  Gln  Pro  Gly  Tyr   Tyr  Gly  Asn  Asp  Ser   Phe  Asn  Tyr  Trp  Ser
                              365                          370                          375                          380
Gly  Asn  Tyr  Val  Ser   Thr  Arg  Pro  Ser  Ile   Gly  Ser  Asn  Asp  Ile   Ile  Thr  Ser  Pro  Phe
                              385                          390                          395                          400
Tyr  Gly  Asn  Lys  Ser   Ser  Glu  Pro  Val  Gln   Asn  Leu  Glu  Phe  Asn   Gly  Glu  Lys  Val  Tyr
                              405                          410                          415                          420
Arg  Ala  Val  Ala  Asn   Thr  Asn  Leu  Ala  Val   Trp  Pro  Ser  Ala  Val   Tyr  Ser  Gly  Val  Thr
                              425                          430                          435                          440
Lys  Val  Glu  Phe  Ser   Gln  Tyr  Asn  Asp  Gln   Thr  Asp  Glu  Ala  Ser   Thr  Gln  Thr  Tyr  Asp
                              445                          450                          455                          460
Ser  Lys  Arg  Asn  Val   Gly  Ala  Val  Ser  Trp   Asp  Ser  Ile  Asp  Gln   Leu  Pro  Pro  Glu  Thr
                              465                          470                          475                          480
Thr  Asp  Glu  Pro  Leu   Glu  Lys  Gly  Tyr  Ser   His  Gln  Leu  Asn  Tyr   Val  Met  Cys  Phe  Leu
                              485                          490                          495                          500
Met  Gln  Gly  Ser  Arg   Gly  Thr  Ile  Pro  Val   Leu  Thr  Trp  Thr  His   Lys  Ser  Val  Asp  Phe
                              505                          510                          515                          520
Phe  Asn  Met  Ile  Asp   Ser  Lys  Lys  Ile  Thr   Gln  Leu  Pro  Leu  Val   Lys  Ala  Tyr  Lys  Leu
                              525                          530                          535                          540
Gln  Ser  Gly  Ala  Ser   Val  Val  Ala  Gly  Pro   Arg  Phe  Thr  Gly  Gly   Asp  Ile  Ile  Gln  Cys
                              545                          550                          555                          560
Thr  Glu  Asn  Gly  Ser   Ala  Ala  Thr  Ile  Tyr   Val  Thr  Pro  Asp  Val   Ser  Tyr  Ser  Gln  Lys
                              565                          570                          575                          580
Tyr  Arg  Ala  Arg  Ile   His  Tyr  Ala  Ser  Thr   Ser  Gln  Ile  Thr  Phe   Thr  Leu  Ser  Leu  Asp
                              585                          590                          595                          600
Gly  Ala  Pro  Phe  Asn   Gln  Tyr  Tyr  Phe  Asp   Lys  Thr  Ile  Asn  Lys   Gly  Asp  Thr  Leu  Thr
                              605                          610                          615                          620
Tyr  Asn  Ser  Phe  Asn   Leu  Ala  Ser  Phe  Ser   Thr  Pro  Phe  Glu  Leu   Ser  Gly  Asn  Asn  Leu
                              625                          630                          635                          640
Gln  Ile  Gly  Val  Thr   Gly  Leu  Ser  Ala  Gly   Asp  Lys  Val  Tyr  Ile   Asp  Lys  Ile  Glu  Phe
Ile  Pro  Val  Asn
```

TABLE 1

Insects Evaluated for Susceptibility to *Bacillus thuringiensis* strain san diego

| Order | Family | Species | Common Name | Stages Tested | Activity |
|---|---|---|---|---|---|
| Coleoptera | Chrysomelidae | *Diabrotica undecimpunctata* | Western spotted cucumber beetle | Adult, larva | + |
| | | *Pyrrhalta luteola* | Elm leaf beetle | Adult, larva | + + + + |
| | | *Haltica tombacina* | — | Adult, larva | + + + |
| | Curculionidae | *Otiorhynchus sulcatus* | Black vine weevil | Larva | + + |
| | Tenebrionidae | *Tenebrio molitor* | Yellow mealworm | Larva | + + |
| | | *Tribolium castaneum* | Red flour beetle | Adult, larva | — |
| | Dermestidae | *Attagenus megatoma* | — | Larva | — |
| | Ptinidae | *Gibbium psylloides* | — | Adult | — |
| Diptera | Culicidae | *Aedes aegypti* | Yellow fever mosquito | Larva | — |
| Lepidoptera | Noctuidae | *Spodoptera exigua* | Beet armyworm | Larva | — |
| | | *Trichoplusia ni* | Cabbage looper | Larva | — |

TABLE 2

Results of 2 Bioassays of *Bacillus thuringiensis* M-7 Against Second Instar *Diabrotica undecimpunctata* U. at 7 Days Post-Inoculation

| Treatment | Avg. no. leaf discs consumed/rep. | % Mortality |
|---|---|---|
| Exp. 1 Control | 3 | 7.5 ± 15.0 |
| 4.3 × 10⁷ spores/ml | <1 | 27.5 ± 9.6 |
| 4.3 × 10⁸ spores/ml | 0 | 62.5 ± 26.3 |
| Exp. 2 Control | 1 | 12.5 ± 12.6 |
| 1 × 10⁶ spores/ml | <1 | 30.0 ± 8.2 |
| 1 × 10⁷ spores/ml | 0 | 50.0 ± 21.6 |

We claim:

1. A recombinant DNA transfer vector comprising DNA having the following nucleotide sequence or equivalent nucleotide sequences containing bases whose translated region codes for the same amino acid sequence:

```
                              ATGA ATCCGAACAA
TCGAAGTGAA CATGATACAA TAAAAACTAC
                    TGAAAATAAT GAGGTGCCAA
CTAACCATGT TCAATATCCT TTAGCGGAAA
                    CTCCAAATCC AACACTAGAA
GATTTAAATT ATAAAGAGTT TTTAAGAATG
                    ACTGCAGATA ATAATACGGA
```

```
AGCACTAGAT AGCTCTACAA CAAAAGATGT
                      CATTCAAAAA GGCATTTCCG
TAGTAGGTGA TCTCCTAGGC GTAGTAGGTT
                      TCCCGTTTGG TGGAGCGCTT
GTTTCGTTTT ATACAAACTT TTTAAATACT
                      ATTTGGCCAA GTGAAGACCC
GTGGAAGGCT TTTATGGAAC AAGTAGAAGC
                      ATTGATGGAT CAGAAAATAG
CTGATTATGC AAAAAATAAA GCTCTTGCAG
                      AGTTACAGGG CCTTCAAAAT
AATGTCGAAG ATTATGTGAG TGCATTGAGT
                      TCATGGCAAA AAAATCCTGT
GAGTTCACGA AATCCACATA GCCAGGGGCG
                      GATAAGAGAG CTGTTTTCTC
AAGCAGAAAG TCATTTTCGT AATTCAATGC
                      CTTCGTTTGC AATTTCTGGA
TACGAGGTTC TATTTCTAAC AACATATGCA
                      CAAGCTGCCA ACACACATTT
ATTTTTACTA AAAGACGCTC AAATTTATGG
                      AGAAGAATGG GGATACGAAA
AAGAAGATAT TGCTGAATTT TATAAAAGAC
                      AACTAAAACT TACGCAAGAA
TATACTGACC ATTGTGTCAA ATGGTATAAT
                      GTTGGATTAG ATAAATTAAG
AGGTTCATCT TATGAATCTT GGGTAAACTT
                      TAACCGTTAT CGCAGAGAGA
TGACATTAAC AGTATTAGAT TTAATTGCAC
                      TATTTCCATT GTATGATGTT
CGGCTATACC CAAAAGAAGT TAAAACCGAA
                      TTAACAAGAG ACGTTTTAAC
AGATCCAATT GTCGGAGTCA ACAACCTTAG
                      GGGCTATGGA ACAACCTTCT
CTAATATAGA AAATTATATT CGAAAACCAC
                      ATCTATTTGA CTATCTGCAT
AGAATTCAAT TTCACACGCG GTTCCAACCA
                      GGATATTATG GAAATGACTC
TTTCAATTAT TGGTCCGGTA ATTATGTTTC
                      AACTAGACCA AGCATAGGAT
CAAATGATAT AATCACATCT CCATTCTATG
                      GAAATAAATC CAGTGAACCT
GTACAAAATT TAGAATTTAA TGGAGAAAAA
                      GTCTATAGAG CCGTAGCAAA
TACAAATCTT GCGGTCTGGC CGTCCGCTGT
                      ATATTCAGGT GTTACAAAAG
TGGAATTTAG CCAATATAAT GATCAAACAG
                      ATGAAGCAAG TACACAAACG
TACGACTCAA AAAGAAATGT TGGCGCGGTC
                      AGCTGGGATT CTATCGATCA
ATTGCCTCCA GAAACAACAG ATGAACCTCT
                      AGAAAAGGGA TATAGCCATC
AACTCAATTA TGTAATGTGC TTTTTAATGC
                      AGGGTAGTAG AGGAACAATC
CCAGTGTTAA CTTGGACACA TAAAAGTGTA
                      GACTTTTTTA ACATGATTGA
TTCGAAAAAA ATTACACAAC TTCCGTTAGT
                      AAAGGCATAT AAGTTACAAT
CTGGTGCTTC CGTTGTCGCA GGTCCTAGGT
                      TTACAGGAGG AGATATCATT
CAATGCACAG AAAATGGAAG TGCGGCAACT
                      ATTTACGTTA CACCGGATGT
GTCGTACTCT CAAAAATATC GAGCTAGAAT
                      TCATTATGCT TCTACATCTC
AGATAACATT TACACTCAGT TTAGACGGGG
                      CACCATTTAA TCAATACTAT
TTCGATAAAA CGATAAATAA AGGAGACACA
                      TTAACGTATA ATTCATTTAA
TTTAGCAAGT TTCAGCACAC CATTCGAATT
                      ATCAGGGAAT AACTTACAAA
TAGGCGTCAC AGGATTAAGT GCTGGAGATA
                      AAGTTTATAT AGACAAAATT
GAATTTATTC CAGTGAAT.
```

2. The DNA transfer vector of claim 1 transferred to and replicated in a prokaryotic microorganism.

3. The DNA transfer vector of claim 2 wherein said prokaryotic microorganism is an E. coli K-12 derivative.

4. A pesticidal composition comprising pesticide-containing substantially intact dead cells having prolonged pesticidal activity when applied to the environment of a target pest, wherein said pesticide is a polypeptide toxic to beetles of the order Coleoptera, is intracellular, and is produced as a result of expression of *Bacillus thuringiensis* strain *san diego* toxin gene in said cell, and an inert carrier, and wherein said *Bacillus thuringiensis* strain *san diego* toxin gene DNA is as follows:

```
                      ATGA ATCCGAACAA
TCGAAGTGAA CATGATACAA TAAAAACTAC
                      TGAAAATAAT GAGGTGCCAA
CTAACCATGT TCAATATCCT TTAGCGGAAA
                      CTCCAAATCC AACACTAGAA
GATTTAAATT ATAAAGAGTT TTTAAGAATG
                      ACTGCAGATA ATAATACGGA
AGCACTAGAT AGCTCTACAA CAAAAGATGT
                      CATTCAAAAA GGCATTTCCG
TAGTAGGTGA TCTCCTAGGC GTAGTAGGTT
                      TCCCGTTTGG TGGAGCGCTT
GTTTCGTTTT ATACAAACTT TTTAAATACT
                      ATTTGGCCAA GTGAAGACCC
GTGGAAGGCT TTTATGGAAC AAGTAGAAGC
                      ATTGATGGAT CAGAAAATAG
CTGATTATGC AAAAAATAAA GCTCTTGCAG
                      AGTTACAGGG CCTTCAAAAT
AATGTCGAAG ATTATGTGAG TGCATTGAGT
                      TCATGGCAAA AAAATCCTGT
GAGTTCACGA AATCCACATA GCCAGGGGCG
                      GATAAGAGAG CTGTTTTCTC
AAGCAGAAAG TCATTTTCGT AATTCAATGC
                      CTTCGTTTGC AATTTCTGGA
TACGAGGTTC TATTTCTAAC AACATATGCA
                      CAAGCTGCCA ACACACATTT
ATTTTTACTA AAAGACGCTC AAATTTATGG
                      AGAAGAATGG GGATACGAAA
AAGAAGATAT TGCTGAATTT TATAAAAGAC
                      AACTAAAACT TACGCAAGAA
TATACTGACC ATTGTGTCAA ATGGTATAAT
                      GTTGGATTAG ATAAATTAAG
AGGTTCATCT TATGAATCTT GGGTAAACTT
                      TAACCGTTAT CGCAGAGAGA
TGACATTAAC AGTATTAGAT TTAATTGCAC
                      TATTTCCATT GTATGATGTT
CGGCTATACC CAAAAGAAGT TAAAACCGAA
                      TTAACAAGAG ACGTTTTAAC
AGATCCAATT GTCGGAGTCA ACAACCTTAG
                      GGGCTATGGA ACAACCTTCT
CTAATATAGA AAATTATATT CGAAAACCAC
                      ATCTATTTGA CTATCTGCAT
AGAATTCAAT TTCACACGCG GTTCCAACCA
                      GGATATTATG GAAATGACTC
TTTCAATTAT TGGTCCGGTA ATTATGTTTC
                      AACTAGACCA AGCATAGGAT
CAAATGATAT AATCACATCT CCATTCTATG
                      GAAATAAATC CAGTGAACCT
GTACAAAATT TAGAATTTAA TGGAGAAAAA
                      GTCTATAGAG CCGTAGCAAA
TACAAATCTT GCGGTCTGGC CGTCCGCTGT
                      ATATTCAGGT GTTACAAAAG
TGGAATTTAG CCAATATAAT GATCAAACAG
                      ATGAAGCAAG TACACAAACG
TACGACTCAA AAAGAAATGT TGGCGCGGTC
                      AGCTGGGATT CTATCGATCA
ATTGCCTCCA GAAACAACAG ATGAACCTCT
                      AGAAAAGGGA TATAGCCATC
AACTCAATTA TGTAATGTGC TTTTTAATGC
                      AGGGTAGTAG AGGAACAATC
CCAGTGTTAA CTTGGACACA TAAAAGTGTA
                      GACTTTTTTA ACATGATTGA
TTCGAAAAAA ATTACACAAC TTCCGTTAGT
                      AAAGGCATAT AAGTTACAAT
CTGGTGCTTC CGTTGTCGCA GGTCCTAGGT
                      TTACAGGAGG AGATATCATT
CAATGCACAG AAAATGGAAG TGCGGCAACT
                      ATTTACGTTA CACCGGATGT
GTCGTACTCT CAAAAATATC GAGCTAGAAT
                      TCATTATGCT TCTACATCTC
AGATAACATT TACACTCAGT TTAGACGGGG
                      CACCATTTAA TCAATACTAT
TTCGATAAAA CGATAAATAA AGGAGACACA
                      TTAACGTATA ATTCATTTAA
TTTAGCAAGT TTCAGCACAC CATTCGAATT
                      ATCAGGGAAT AACTTACAAA
```

-continued

```
TAGGCGTCAC AGGATTAAGT GCTGGAGATA
                      AAGTTTATAT AGACAAAATT
GAATTTATTC CAGTGAAT.
``` and equivalent nucleotide sequences coding for molecules with the following amino acid sequence:

| Met | Asn | Pro | Asn | Asn 5 | Arg | Ser | Glu | His | Asp 10 |
|---|---|---|---|---|---|---|---|---|---|
| Thr | Ile | Lys | Thr | Thr 15 | Glu | Asn | Asn | Glu | Val 20 |
| Pro | Thr | Asn | His | Val 25 | Gln | Tyr | Pro | Leu | Ala 30 |
| Glu | Thr | Pro | Asn | Pro 35 | Thr | Leu | Glu | Asp | Leu 40 |
| Asn | Tyr | Lys | Glu | Phe 45 | Leu | Arg | Met | Thr | Ala 50 |
| Asp | Asn | Asn | Thr | Glu 55 | Ala | Leu | Asp | Ser | Ser 60 |
| Thr | Thr | Lys | Asp | Val 65 | Ile | Gln | Lys | Gly | Ile 70 |
| Ser | Val | Val | Gly | Asp 75 | Leu | Leu | Gly | Val | Val 80 |
| Gly | Phe | Pro | Phe | Gly 85 | Gly | Ala | Leu | Val | Ser 90 |
| Phe | Tyr | Thr | Asn | Phe 95 | Leu | Asn | Thr | Ile | Trp 100 |
| Pro | Ser | Glu | Asp | Pro 105 | Trp | Lys | Ala | Phe | Met 110 |
| Glu | Gln | Val | Glu | Ala 115 | Leu | Met | Asp | Gln | Lys 120 |
| Ile | Ala | Asp | Tyr | Ala 125 | Lys | Asn | Lys | Ala | Leu 130 |
| Ala | Glu | Leu | Gln | Gly 135 | Leu | Gln | Asn | Asn | Val 140 |
| Glu | Asp | Tyr | Val | Ser 145 | Ala | Leu | Ser | Ser | Trp 150 |
| Gln | Lys | Asn | Pro | Val 155 | Ser | Ser | Arg | Asn | Pro 160 |
| His | Ser | Gln | Gly | Arg 165 | Ile | Arg | Glu | Leu | Phe 170 |
| Ser | Gln | Ala | Glu | Ser 175 | His | Phe | Arg | Asn | Ser 180 |
| Met | Pro | Ser | Phe | Ala 185 | Ile | Ser | Gly | Tyr | Glu 190 |
| Val | Leu | Phe | Leu | Thr 195 | Thr | Tyr | Ala | Gln | Ala 200 |
| Ala | Asn | Thr | His | Leu 205 | Phe | Leu | Leu | Lys | Asp 210 |
| Ala | Gln | Ile | Tyr | Gly 215 | Glu | Glu | Trp | Gly | Tyr 220 |
| Glu | Lys | Glu | Asp | Ile 225 | Ala | Glu | Phe | Tyr | Lys 230 |
| Arg | Gln | Leu | Lys | Leu 235 | Thr | Gln | Glu | Tyr | Thr 240 |
| Asp | His | Cys | Val | Lys 245 | Trp | Tyr | Asn | Val | Gly 250 |
| Leu | Asp | Lys | Leu | Arg 255 | Gly | Ser | Ser | Tyr | Glu 260 |
| Ser | Trp | Val | Asn | Phe 265 | Asn | Arg | Tyr | Arg | Arg 270 |
| Glu | Met | Thr | Leu | Thr 275 | Val | Leu | Asp | Leu | Ile 280 |
| Ala | Leu | Phe | Pro | Leu 285 | Tyr | Asp | Val | Arg | Leu 290 |
| Tyr | Pro | Lys | Glu | Val 295 | Lys | Thr | Glu | Leu | Thr 300 |
| Arg | Asp | Val | Leu | Thr 305 | Asp | Pro | Ile | Val | Gly 310 |
| Val | Asn | Asn | Leu | Arg 315 | Gly | Tyr | Gly | Thr | Thr 320 |
| Phe | Ser | Asn | Ile | Glu 325 | Asn | Tyr | Ile | Arg | Lys 330 |
| Pro | His | Leu | Phe | Asp 335 | Tyr | Leu | His | Arg | Ile 340 |
| Gln | Phe | His | Thr | Arg 345 | Phe | Gln | Pro | Gly | Tyr 350 |
| Tyr | Gly | Asn | Asp | Ser 355 | Phe | Asn | Tyr | Trp | Ser 360 |
| Gly | Asn | Tyr | Val | Ser 365 | Thr | Arg | Pro | Ser | Ile 370 |
| Gly | Ser | Asn | Asp | Ile 375 | Ile | Thr | Ser | Pro | Phe 380 |
| Tyr | Gly | Asn | Lys | Ser 385 | Ser | Glu | Pro | Val | Gln 390 |
| Asn | Leu | Glu | Phe | Asn 395 | Gly | Glu | Lys | Val | Tyr 400 |
| Arg | Ala | Val | Ala | Asn 405 | Thr | Asn | Leu | Ala | Val 410 |
| Trp | Pro | Ser | Ala | Val 415 | Tyr | Ser | Gly | Val | Thr 420 |
| Lys | Val | Glu | Phe | Ser 425 | Gln | Tyr | Asn | Asp | Gln 430 |
| Thr | Asp | Glu | Ala | Ser 435 | Thr | Gln | Thr | Tyr | Asp 440 |
| Ser | Lys | Arg | Asn | Val 445 | Gly | Ala | Val | Ser | Trp 450 |
| Asp | Ser | Ile | Asp | Gln 455 | Leu | Pro | Pro | Glu | Thr 460 |
| Thr | Asp | Glu | Pro | Leu 465 | Glu | Lys | Gly | Tyr | Ser 470 |
| His | Gln | Leu | Asn | Tyr 475 | Val | Met | Cys | Phe | Leu 480 |
| Met | Gln | Gly | Ser | Arg 485 | Gly | Thr | Ile | Pro | Val 490 |
| Leu | Thr | Trp | Thr | His 495 | Lys | Ser | Val | Asp | Phe 500 |
| Phe | Asn | Met | Ile | Asp 505 | Ser | Lys | Lys | Ile | Thr 510 |
| Gln | Leu | Pro | Leu | Val 515 | Lys | Ala | Tyr | Lys | Leu 520 |
| Gln | Ser | Gly | Ala | Ser 525 | Val | Val | Ala | Gly | Pro 530 |
| Arg | Phe | Thr | Gly | Gly 535 | Asp | Ile | Ile | Gln | Cys 540 |
| Thr | Glu | Asn | Gly | Ser 545 | Ala | Ala | Thr | Ile | Tyr 550 |
| Val | Thr | Pro | Asp | Val 555 | Ser | Tyr | Ser | Gln | Lys 560 |
| Tyr | Arg | Ala | Arg | Ile 565 | His | Tyr | Ala | Ser | Thr 570 |
| Ser | Gln | Ile | Thr | Phe 575 | Thr | Leu | Ser | Leu | Asp 580 |
| Gly | Ala | Pro | Phe | Asn 585 | Gln | Tyr | Tyr | Phe | Asp 590 |
| Lys | Thr | Ile | Asn | Lys 595 | Gly | Asp | Thr | Leu | Thr 600 |
| Tyr | Asn | Ser | Phe | Asn 605 | Leu | Ala | Ser | Phe | Ser 610 |
| Thr | Pro | Phe | Glu | Leu 615 | Ser | Gly | Asn | Asn | Leu 620 |
| Gln | Ile | Gly | Val | Thr 625 | Gly | Leu | Ser | Ala | Gly 630 |
| Asp | Lys | Val | Tyr | Ile 635 | Asp | Lys | Ile | Glu | Phe 640 |
| Ile | Pro | Val | Asn. | | | | | | |

5. A method of protecting plants against beetles of the order Coleoptera which comprises applying to said plants an effective amount of a pesticidal composition comprising pesticide-containing substantially intact dead unicellular microorganisms, wherein said pesticide is intracellular and is produced as a result of expression of a *Bacillus thuringiensis* toxin gene toxic to beetles of the order Coleoptera in said cell, and an inert carrier, and said microorganism is killed under conditions which prolong the pesticidal activity when said composition is applied to the environment of a target pest, and wherein said *Bacillus thuringiensis* toxin gene DNA is as follows:

```
                              ATGA ATCCGAACAA
TCGAAGTGAA CATGATACAA TAAAAACTAC
                     TGAAAATAAT GAGGTGCCAA
CTAACCATGT TCAATATCCT TTAGCGGAAA
                     CTCCAAATCC AACACTAGAA
GATTTAAATT ATAAAGAGTT TTTAAGAATG
```

```
            ACTGCAGATA ATAATACGGA
AGCACTAGAT AGCTCTACAA CAAAAGATGT
            CATTCAAAAA GGCATTTCCG
TAGTAGGTGA TCTCCTAGGC GTAGTAGGTT
            TCCCGTTTGG TGGAGCGCTT
GTTTCGTTTT ATACAAACTT TTTAAATACT
            ATTTGGCCAA GTGAAGACCC
GTGGAAGGCT TTTATGGAAC AAGTAGAAGC
            ATTGATGGAT CAGAAAATAG
CTGATTATGC AAAAAATAAA GCTCTTGCAG
            AGTTACAGGG CCTTCAAAAT
AATGTCGAAG ATTATGTGAG TGCATTGAGT
            TCATGGCAAA AAAATCCTGT
GAGTTCACGA AATCCACATA GCCAGGGGCG
            GATAAGAGAG CTGTTTTCTC
AAGCAGAAAG TCATTTTCGT AATTCAATGC
            CTTCGTTTGC AATTTCTGGA
TACGAGGTTC TATTTCTAAC AACATATGCA
            CAAGCTGCCA ACACACATTT
ATTTTTACTA AAAGACGCTC AAATTTATGG
            AGAAGAATGG GGATACGAAA
AAGAAGATAT TGCTGAATTT TATAAAAGAC
            AACTAAAACT TACGCAAGAA
TATACTGACC ATTGTGTCAA ATGGTATAAT
            GTTGGATTAG ATAAATTAAG
AGGTTCATCT TATGAATCTT GGGTAAACTT
            TAACCGTTAT CGCAGAGAGA
TGACATTAAC AGTATTAGAT TTAATTGCAC
            TATTTCCATT GTATGATGTT
CGGCTATACC CAAAAGAAGT TAAAACCGAA
            TTAACAAGAG ACGTTTTAAC
AGATCCAATT GTCGGAGTCA ACAACCTTAG
            GGGCTATGGA ACAACCTTCT
CTAATATAGA AAATTATATT CGAAAACCAC
            ATCTATTTGA CTATCTGCAT
AGAATTCAAT TTCACACGCG GTTCCAACCA
            GGATATTATG GAAATGACTC
TTTCAATTAT TGGTCCGGTA ATTATGTTTC
            AACTAGACCA AGCATAGGAT
CAAATGATAT AATCACATCT CCATTCTATG
            GAAATAAATC CAGTGAACCT
GTACAAAATT TAGAATTTAA TGGAGAAAAA
            GTCTATAGAG CCGTAGCAAA
TACAAATCTT GCGGTCTGGC CGTCCGCTGT
            ATATTCAGGT GTTACAAAAG
TGGAATTTAG CCAATATAAT GATCAAACAG
            ATGAAGCAAG TACACAAACG
TACGACTCAA AAAGAAATGT TGGCGCGGTC
            AGCTGGGATT CTATCGATCA
ATTGCCTCCA GAAACAACAG ATGAACCTCT
            AGAAAAGGGA TATAGCCATC
AACTCAATTA TGTAATGTGC TTTTTAATGC
            AGGGTAGTAG AGGAACAATC
CCAGTGTTAA CTTGGACACA TAAAAGTGTA
            GACTTTTTTA ACATGATTGA
TTCGAAAAAA ATTACACAAC TTCCGTTAGT
            AAAGGCATAT AAGTTACAAT
CTGGTGCTTC CGTTGTCGCA GGTCCTAGGT
            TTACAGGAGG AGATATCATT
CAATGCACAG AAAATGGAAG TGCGGCAACT
            ATTTACGTTA CACCGGATGT
GTCGTACTCT CAAAAATATC GAGCTAGAAT
            TCATTATGCT TCTACATCTC
AGATAACATT TACACTCAGT TTAGACGGGG
            CACCATTTAA TCAATACTAT
TTCGATAAAA CGATAAATAA AGGAGACACA
            TTAACGTATA ATTCATTTAA
TTTAGCAAGT TTCAGCACAC CATTCGAATT
            ATCAGGGAAT AACTTACAAA
TAGGCGTCAC AGGATTAAGT GCTGGAGATA
            AAGTTTATAT AGACAAAATT
GAATTTATTC CAGTGAAT
``` and equivalent nucleotide sequences coding for molecules with the following amino acid sequence;

|   |   |   | 5 |   |   |   |   |   | 10 |
|---|---|---|---|---|---|---|---|---|---|
| Met | Asn | Pro | Asn | Asn | Arg | Ser | Glu | His | Asp |
|   |   |   | 15 |   |   |   |   |   | 20 |
| Thr | Ile | Lys | Thr | Thr | Glu | Asn | Asn | Glu | Val |
|   |   |   | 25 |   |   |   |   |   | 30 |
| Pro | Thr | Asn | His | Val | Gln | Tyr | Pro | Leu | Ala |
|   |   |   | 35 |   |   |   |   |   | 40 |
| Glu | Thr | Pro | Asn | Pro | Thr | Leu | Glu | Asp | Leu |
|   |   |   | 45 |   |   |   |   |   | 50 |
| Asn | Tyr | Lys | Glu | Phe | Leu | Arg | Met | Thr | Ala |
|   |   |   | 55 |   |   |   |   |   | 60 |
| Asp | Asn | Asn | Thr | Glu | Ala | Leu | Asp | Ser | Ser |
|   |   |   | 65 |   |   |   |   |   | 70 |
| Thr | Thr | Lys | Asp | Val | Ile | Gln | Lys | Gly | Ile |
|   |   |   | 75 |   |   |   |   |   | 80 |
| Ser | Val | Val | Gly | Asp | Leu | Leu | Gly | Val | Val |
|   |   |   | 85 |   |   |   |   |   | 90 |
| Gly | Phe | Pro | Phe | Gly | Gly | Ala | Leu | Val | Ser |
|   |   |   | 95 |   |   |   |   |   | 100 |
| Phe | Tyr | Thr | Asn | Phe | Leu | Asn | Thr | Ile | Trp |
|   |   |   | 105 |   |   |   |   |   | 110 |
| Pro | Ser | Glu | Asp | Pro | Trp | Lys | Ala | Phe | Met |
|   |   |   | 115 |   |   |   |   |   | 120 |
| Glu | Gln | Val | Glu | Ala | Leu | Met | Asp | Gln | Lys |
|   |   |   | 125 |   |   |   |   |   | 130 |
| Ile | Ala | Asp | Tyr | Ala | Lys | Asn | Lys | Ala | Leu |
|   |   |   | 135 |   |   |   |   |   | 140 |
| Ala | Glu | Leu | Gln | Gly | Leu | Gln | Asn | Asn | Val |
|   |   |   | 145 |   |   |   |   |   | 150 |
| Glu | Asp | Tyr | Val | Ser | Ala | Leu | Ser | Ser | Trp |
|   |   |   | 155 |   |   |   |   |   | 160 |
| Gln | Lys | Asn | Pro | Val | Ser | Ser | Arg | Asn | Pro |
|   |   |   | 165 |   |   |   |   |   | 170 |
| His | Ser | Gln | Gly | Arg | Ile | Arg | Glu | Leu | Phe |
|   |   |   | 175 |   |   |   |   |   | 180 |
| Ser | Gln | Ala | Glu | Ser | His | Phe | Arg | Asn | Ser |
|   |   |   | 185 |   |   |   |   |   | 190 |
| Met | Pro | Ser | Phe | Ala | Ile | Ser | Gly | Tyr | Glu |
|   |   |   | 195 |   |   |   |   |   | 200 |
| Val | Leu | Phe | Leu | Thr | Thr | Tyr | Ala | Gln | Ala |
|   |   |   | 205 |   |   |   |   |   | 210 |
| Ala | Asn | Thr | His | Leu | Phe | Leu | Leu | Lys | Asp |
|   |   |   | 215 |   |   |   |   |   | 220 |
| Ala | Gln | Ile | Tyr | Gly | Glu | Glu | Trp | Gly | Tyr |
|   |   |   | 225 |   |   |   |   |   | 230 |
| Glu | Lys | Glu | Asp | Ile | Ala | Glu | Phe | Tyr | Lys |
|   |   |   | 235 |   |   |   |   |   | 240 |
| Arg | Gln | Leu | Lys | Leu | Thr | Gln | Glu | Tyr | Thr |
|   |   |   | 245 |   |   |   |   |   | 250 |
| Asp | His | Cys | Val | Lys | Trp | Tyr | Asn | Val | Gly |
|   |   |   | 255 |   |   |   |   |   | 260 |
| Leu | Asp | Lys | Leu | Arg | Gly | Ser | Ser | Tyr | Glu |
|   |   |   | 265 |   |   |   |   |   | 270 |
| Ser | Trp | Val | Asn | Phe | Asn | Arg | Tyr | Arg | Arg |
|   |   |   | 275 |   |   |   |   |   | 280 |
| Glu | Met | Thr | Leu | Thr | Val | Leu | Asp | Leu | Ile |
|   |   |   | 285 |   |   |   |   |   | 290 |
| Ala | Leu | Phe | Pro | Leu | Tyr | Asp | Val | Arg | Leu |
|   |   |   | 295 |   |   |   |   |   | 300 |
| Tyr | Pro | Lys | Glu | Val | Lys | Thr | Glu | Leu | Thr |
|   |   |   | 305 |   |   |   |   |   | 310 |
| Arg | Asp | Val | Leu | Thr | Asp | Pro | Ile | Val | Gly |
|   |   |   | 315 |   |   |   |   |   | 320 |
| Val | Asn | Asn | Leu | Arg | Gly | Tyr | Gly | Thr | Thr |
|   |   |   | 325 |   |   |   |   |   | 330 |
| Phe | Ser | Asn | Ile | Glu | Asn | Tyr | Ile | Arg | Lys |
|   |   |   | 335 |   |   |   |   |   | 340 |
| Pro | His | Leu | Phe | Asp | Tyr | Leu | His | Arg | Ile |
|   |   |   | 345 |   |   |   |   |   | 350 |
| Gln | Phe | His | Thr | Arg | Phe | Gln | Pro | Gly | Tyr |
|   |   |   | 355 |   |   |   |   |   | 360 |
| Tyr | Gly | Asn | Asp | Ser | Phe | Asn | Tyr | Trp | Ser |
|   |   |   | 365 |   |   |   |   |   | 370 |
| Gly | Asn | Tyr | Val | Ser | Thr | Arg | Pro | Ser | Ile |
|   |   |   | 375 |   |   |   |   |   | 380 |
| Gly | Ser | Asn | Asp | Ile | Ile | Thr | Ser | Pro | Phe |
|   |   |   | 385 |   |   |   |   |   | 390 |
| Tyr | Gly | Asn | Lys | Ser | Ser | Glu | Pro | Val | Gln |
|   |   |   | 395 |   |   |   |   |   | 400 |
| Asn | Leu | Glu | Phe | Asn | Gly | Glu | Lys | Val | Tyr |
|   |   |   | 405 |   |   |   |   |   | 410 |
| Arg | Ala | Val | Ala | Asn | Thr | Asn | Leu | Ala | Val |
|   |   |   | 415 |   |   |   |   |   | 420 |
| Trp | Pro | Ser | Ala | Val | Tyr | Ser | Gly | Val | Thr |
|   |   |   | 425 |   |   |   |   |   | 430 |
| Lys | Val | Glu | Phe | Ser | Gln | Tyr | Asn | Asp | Gln |

-continued

| | | | | 435 | | | | | 440 |
|---|---|---|---|---|---|---|---|---|---|
| Thr | Asp | Glu | Ala | Ser | Thr | Gln | Thr | Tyr | Asp |
| | | | | 445 | | | | | 450 |
| Ser | Lys | Arg | Asn | Val | Gly | Ala | Val | Ser | Trp |
| | | | | 455 | | | | | 460 |
| Asp | Ser | Ile | Asp | Gln | Leu | Pro | Pro | Glu | Thr |
| | | | | 465 | | | | | 470 |
| Thr | Asp | Glu | Pro | Leu | Glu | Lys | Gly | Tyr | Ser |
| | | | | 475 | | | | | 480 |
| His | Gln | Leu | Asn | Tyr | Val | Met | Cys | Phe | Leu |
| | | | | 485 | | | | | 490 |
| Met | Gln | Gly | Ser | Arg | Gly | Thr | Ile | Pro | Val |
| | | | | 495 | | | | | 500 |
| Leu | Thr | Trp | Thr | His | Lys | Ser | Val | Asp | Phe |
| | | | | 505 | | | | | 510 |
| Phe | Asn | Met | Ile | Asp | Ser | Lys | Lys | Ile | Thr |
| | | | | 515 | | | | | 520 |
| Gln | Leu | Pro | Leu | Val | Lys | Ala | Tyr | Lys | Leu |
| | | | | 525 | | | | | 530 |
| Gln | Ser | Gly | Ala | Ser | Val | Val | Ala | Gly | Pro |
| | | | | 535 | | | | | 540 |
| Arg | Phe | Thr | Gly | Gly | Asp | Ile | Ile | Gln | Cys |
| | | | | 545 | | | | | 550 |
| Thr | Glu | Asn | Gly | Ser | Ala | Ala | Thr | Ile | Tyr |
| | | | | 555 | | | | | 560 |
| Val | Thr | Pro | Asp | Val | Ser | Tyr | Ser | Gln | Lys |
| | | | | 565 | | | | | 570 |
| Tyr | Arg | Ala | Arg | Ile | His | Tyr | Ala | Ser | Thr |
| | | | | 575 | | | | | 580 |
| Ser | Gln | Ile | Thr | Phe | Thr | Leu | Ser | Leu | Asp |
| | | | | 585 | | | | | 590 |
| Gly | Ala | Pro | Phe | Asn | Gln | Tyr | Tyr | Phe | Asp |
| | | | | 595 | | | | | 600 |
| Lys | Thr | Ile | Asn | Lys | Gly | Asp | Thr | Leu | Thr |
| | | | | 605 | | | | | 610 |
| Tyr | Asn | Ser | Phe | Asn | Leu | Ala | Ser | Phe | Ser |
| | | | | 615 | | | | | 620 |
| Thr | Pro | Phe | Glu | Leu | Ser | Gly | Asn | Asn | Leu |
| | | | | 625 | | | | | 630 |
| Gln | Ile | Gly | Val | Thr | Gly | Leu | Ser | Ala | Gly |
| | | | | 635 | | | | | 640 |
| Asp | Lys | Val | Tyr | Ile | Asp | Lys | Ile | Glu | Phe |
| Ile | Pro | Val | Asn. | | | | | | |

6. Microbial cells which are dead substantially intact unicellular microorganism cells containing an intracellular toxin, which toxin is a result of expression of a *Bacillus thuringiensis* toxin gene toxic to beetles of the order Coleoptera, wherein said cells are killed under conditions which inactivate enzymes and prolong the pesticidal activity when said cell is applied to the environment of a target pest, and wherein said *Bacillus thuringiensis* toxin gene DNA is as follows:

```
                                    ATGA ATCCGAACAA
TCGAAGTGAA CATGATACAA TAAAAACTAC
                    TGAAAATAAT GAGGTGCCAA
CTAACCATGT TCAATATCCT TTAGCGGAAA
                    CTCCAAATCC AACACTAGAA
GATTTAAATT ATAAAGAGTT TTTAAGAATG
                    ACTGCAGATA ATAATACGGA
AGCACTAGAT AGCTCTACAA CAAAAGATGT
                    CATTCAAAAA GGCATTTCCG
TAGTAGGTGA TCTCCTAGGC GTAGTAGGTT
                    TCCCGTTTGG TGGAGCGCTT
GTTTCGTTTT ATACAAACTT TTTAAATACT
                    ATTTGGCCAA GTGAAGACCC
GTGGAAGGCT TTTATGGAAC AAGTAGAAGC
                    ATTGATGGAT CAGAAAATAG
CTGATTATGC AAAAAATAAA GCTCTTGCAG
                    AGTTACAGGG CCTTCAAAAT
AATGTCGAAG ATTATGTGAG TGCATTGAGT
                    TCATGGCAAA AAAATCCTGT
GAGTTCACGA AATCCACATA GCCAGGGGCG
                    GATAAGAGAG CTGTTTTCTC
AAGCAGAAAG TCATTTTCGT AATTCAATGC
                    CTTCGTTTGC AATTTCTGGA
TACGAGGTTC TATTTCTAAC AACATATGCA
                                    CAAGCTGCCA ACACACATTT
ATTTTTACTA AAAGACGCTC AAATTTATGG
                                    AGAAGAATGG GGATACGAAA
AAGAAGATAT TGCTGAATTT TATAAAAGAC
                                    AACTAAAACT TACGCAAGAA
TATACTGACC ATTGTGTCAA ATGGTATAAT
                                    GTTGGATTAG ATAAATTAAG
AGGTTCATCT TATGAATCTT GGGTAAACTT
                                    TAACCGTTAT CGCAGAGAGA
TGACATTAAC AGTATTAGAT TTAATTGCAC
                                    TATTTCCATT GTATGATGTT
CGGCTATACC CAAAAGAAGT TAAAACCGAA
                                    TTAACAAGAG ACGTTTTAAC
AGATCCAATT GTCGGAGTCA ACAACCTTAG
                                    GGGCTATGGA ACAACCTTCT
CTAATATAGA AAATTATATT CGAAAACCAC
                                    ATCTATTTGA CTATCTGCAT
AGAATTCAAT TTCACACGCG GTTCCAACCA
                                    GGATATTATG GAAATGACTC
TTTCAATTAT TGGTCCGGTA ATTATGTTTC
                                    AACTAGACCA AGCATAGGAT
CAAATGATAT AATCACATCT CCATTCTATG
                                    GAAATAAATC CAGTGAACCT
GTACAAAATT TAGAATTTAA TGGAGAAAAA
                                    GTCTATAGAG CCGTAGCAAA
TACAAATCTT GCGGTCTGGC CGTCCGCTGT
                                    ATATTCAGGT GTTACAAAAG
TGGAATTTAG CCAATATAAT GATCAAACAG
                                    ATGAAGCAAG TACACAAACG
TACGACTCAA AAAGAAATGT TGGCGCGGTC
                                    AGCTGGGATT CTATCGATCA
ATTGCCTCCA GAAACAACAG ATGAACCTCT
                                    AGAAAAGGGA TATAGCCATC
AACTCAATTA TGTAATGTGC TTTTTAATGC
                                    AGGGTAGTAG AGGAACAATC
CCAGTGTTAA CTTGGACACA TAAAAGTGTA
                                    GACTTTTTTA ACATGATTGA
TTCGAAAAAA ATTACACAAC TTCCGTTAGT
                                    AAAGGCATAT AAGTTACAAT
CTGGTGCTTC CGTTGTCGCA GGTCCTAGGT
                                    TTACAGGAGG AGATATCATT
CAATGCACAG AAAATGGAAG TGCGGCAACT
                                    ATTTACGTTA CACCGGATGT
GTCGTACTCT CAAAAATATC GAGCTAGAAT
                                    TCATTATGCT TCTACATCTC
AGATAACATT TACACTCAGT TTAGACGGGG
                                    CACCATTTAA TCAATACTAT
TTCGATAAAA CGATAAATAA AGGAGACACA
                                    TTAACGTATA ATTCATTTAA
TTTAGCAAGT TTCAGCACAC CATTCGAATT
                                    ATCAGGGAAT AACTTACAAA
TAGGCGTCAC AGGATTAAGT GCTGGAGATA
                                    AAGTTTATAT AGACAAAATT
GAATTTATTC CAGTGAAT.
``` and equivalent nucleotide sequences coding for molecules with the following amino acid sequence;

| | | | | 5 | | | | | 10 |
|---|---|---|---|---|---|---|---|---|---|
| Met | Asn | Pro | Asn | Asn | Arg | Ser | Glu | His | Asp |
| | | | | 15 | | | | | 20 |
| Thr | Ile | Lys | Thr | Thr | Glu | Asn | Asn | Glu | Val |
| | | | | 25 | | | | | 30 |
| Pro | Thr | Asn | His | Val | Gln | Tyr | Pro | Leu | Ala |
| | | | | 35 | | | | | 40 |
| Glu | Thr | Pro | Asn | Pro | Thr | Leu | Glu | Asp | Leu |
| | | | | 45 | | | | | 50 |
| Asn | Tyr | Lys | Glu | Phe | Leu | Arg | Met | Thr | Ala |
| | | | | 55 | | | | | 60 |
| Asp | Asn | Asn | Thr | Glu | Ala | Leu | Asp | Ser | Ser |
| | | | | 65 | | | | | 70 |
| Thr | Thr | Lys | Asp | Val | Ile | Gln | Lys | Gly | Ile |
| | | | | 75 | | | | | 80 |
| Ser | Val | Val | Gly | Asp | Leu | Leu | Gly | Val | Val |
| | | | | 85 | | | | | 90 |
| Gly | Phe | Pro | Phe | Gly | Gly | Ala | Leu | Val | Ser |
| | | | | 95 | | | | | 100 |
| Phe | Tyr | Thr | Asn | Phe | Leu | Asn | Thr | Ile | Trp |
| | | | | 105 | | | | | 110 |
| Pro | Ser | Glu | Asp | Pro | Trp | Lys | Ala | Phe | Met |

-continued

| | | | | 115 | | | | | 120 |
|---|---|---|---|---|---|---|---|---|---|
| Glu | Gln | Val | Glu | Ala | Leu | Met | Asp | Gln | Lys |
| | | | | 125 | | | | | 130 |
| Ile | Ala | Asp | Tyr | Ala | Lys | Asn | Lys | Ala | Leu |
| | | | | 135 | | | | | 140 |
| Ala | Glu | Leu | Gln | Gly | Leu | Gln | Asn | Asn | Val |
| | | | | 145 | | | | | 150 |
| Glu | Asp | Tyr | Val | Ser | Ala | Leu | Ser | Ser | Trp |
| | | | | 155 | | | | | 160 |
| Gln | Lys | Asn | Pro | Val | Ser | Ser | Arg | Asn | Pro |
| | | | | 165 | | | | | 170 |
| His | Ser | Gln | Gly | Arg | Ile | Arg | Glu | Leu | Phe |
| | | | | 175 | | | | | 180 |
| Ser | Gln | Ala | Glu | Ser | His | Phe | Arg | Asn | Ser |
| | | | | 185 | | | | | 190 |
| Met | Pro | Ser | Phe | Ala | Ile | Ser | Gly | Tyr | Glu |
| | | | | 195 | | | | | 200 |
| Val | Leu | Phe | Leu | Thr | Thr | Tyr | Ala | Gln | Ala |
| | | | | 205 | | | | | 210 |
| Ala | Asn | Thr | His | Leu | Phe | Leu | Leu | Lys | Asp |
| | | | | 215 | | | | | 220 |
| Ala | Gln | Ile | Tyr | Gly | Glu | Glu | Trp | Gly | Tyr |
| | | | | 225 | | | | | 230 |
| Glu | Lys | Glu | Asp | Ile | Ala | Glu | Phe | Tyr | Lys |
| | | | | 235 | | | | | 240 |
| Arg | Gln | Leu | Lys | Leu | Thr | Gln | Glu | Tyr | Thr |
| | | | | 245 | | | | | 250 |
| Asp | His | Cys | Val | Lys | Trp | Tyr | Asn | Val | Gly |
| | | | | 255 | | | | | 260 |
| Leu | Asp | Lys | Leu | Arg | Gly | Ser | Ser | Tyr | Glu |
| | | | | 265 | | | | | 270 |
| Ser | Trp | Val | Asn | Phe | Asn | Arg | Tyr | Arg | Arg |
| | | | | 275 | | | | | 280 |
| Glu | Met | Thr | Leu | Thr | Val | Leu | Asp | Leu | Ile |
| | | | | 285 | | | | | 290 |
| Ala | Leu | Phe | Pro | Leu | Tyr | Asp | Val | Arg | Leu |
| | | | | 295 | | | | | 300 |
| Tyr | Pro | Lys | Glu | Val | Lys | Thr | Glu | Leu | Thr |
| | | | | 305 | | | | | 310 |
| Arg | Asp | Val | Leu | Thr | Asp | Pro | Ile | Val | Gly |
| | | | | 315 | | | | | 320 |
| Val | Asn | Asn | Leu | Arg | Gly | Tyr | Gly | Thr | Thr |
| | | | | 325 | | | | | 330 |
| Phe | Ser | Asn | Ile | Glu | Asn | Tyr | Ile | Arg | Lys |
| | | | | 335 | | | | | 340 |
| Pro | His | Leu | Phe | Asp | Tyr | Leu | His | Arg | Ile |
| | | | | 345 | | | | | 350 |
| Gln | Phe | His | Thr | Arg | Phe | Gln | Pro | Gly | Tyr |
| | | | | 355 | | | | | 360 |
| Tyr | Gly | Asn | Asp | Ser | Phe | Asn | Tyr | Trp | Ser |
| | | | | 365 | | | | | 370 |
| Gly | Asn | Tyr | Val | Ser | Thr | Arg | Pro | Ser | Ile |
| | | | | 375 | | | | | 380 |
| Gly | Ser | Asn | Asp | Ile | Ile | Thr | Ser | Pro | Phe |
| | | | | 385 | | | | | 390 |
| Tyr | Gly | Asn | Lys | Ser | Ser | Glu | Pro | Val | Gln |
| | | | | 395 | | | | | 400 |
| Asn | Leu | Glu | Phe | Asn | Gly | Glu | Lys | Val | Tyr |
| | | | | 405 | | | | | 410 |
| Arg | Ala | Val | Ala | Asn | Thr | Asn | Leu | Ala | Val |
| | | | | 415 | | | | | 420 |
| Trp | Pro | Ser | Ala | Val | Tyr | Ser | Gly | Val | Thr |
| | | | | 425 | | | | | 430 |
| Lys | Val | Glu | Phe | Ser | Gln | Tyr | Asn | Asp | Gln |
| | | | | 435 | | | | | 440 |
| Thr | Asp | Glu | Ala | Ser | Thr | Gln | Thr | Tyr | Asp |
| | | | | 445 | | | | | 450 |
| Ser | Lys | Arg | Asn | Val | Gly | Ala | Val | Ser | Trp |
| | | | | 455 | | | | | 460 |
| Asp | Ser | Ile | Asp | Gln | Leu | Pro | Pro | Glu | Thr |
| | | | | 465 | | | | | 470 |
| Thr | Asp | Glu | Pro | Leu | Glu | Lys | Gly | Tyr | Ser |
| | | | | 475 | | | | | 480 |
| His | Gln | Leu | Asn | Tyr | Val | Met | Cys | Phe | Leu |
| | | | | 485 | | | | | 490 |
| Met | Gln | Gly | Ser | Arg | Gly | Thr | Ile | Pro | Val |
| | | | | 495 | | | | | 500 |
| Leu | Thr | Trp | Thr | His | Lys | Ser | Val | Asp | Phe |
| | | | | 505 | | | | | 510 |
| Phe | Asn | Met | Ile | Asp | Ser | Lys | Lys | Ile | Thr |
| | | | | 515 | | | | | 520 |
| Gln | Leu | Pro | Leu | Val | Lys | Ala | Tyr | Lys | Leu |
| | | | | 525 | | | | | 530 |
| Gln | Ser | Gly | Ala | Ser | Val | Val | Ala | Gly | Pro |
| | | | | 535 | | | | | 540 |
| Arg | Phe | Thr | Gly | Gly | Asp | Ile | Ile | Gln | Cys |
| | | | | 545 | | | | | 550 |
| Thr | Glu | Asn | Gly | Ser | Ala | Ala | Thr | Ile | Tyr |
| | | | | 555 | | | | | 560 |
| Val | Thr | Pro | Asp | Val | Ser | Tyr | Ser | Gln | Lys |
| | | | | 565 | | | | | 570 |
| Tyr | Arg | Ala | Arg | Ile | His | Tyr | Ala | Ser | Thr |
| | | | | 575 | | | | | 580 |
| Ser | Gln | Ile | Thr | Phe | Thr | Leu | Ser | Leu | Asp |
| | | | | 585 | | | | | 590 |
| Gly | Ala | Pro | Phe | Asn | Gln | Tyr | Tyr | Phe | Asp |
| | | | | 595 | | | | | 600 |
| Lys | Thr | Ile | Asn | Lys | Gly | Asp | Thr | Leu | Thr |
| | | | | 605 | | | | | 610 |
| Tyr | Asn | Ser | Phe | Asn | Leu | Ala | Ser | Phe | Ser |
| | | | | 615 | | | | | 620 |
| Thr | Pro | Phe | Glu | Leu | Ser | Gly | Asn | Asn | Leu |
| | | | | 625 | | | | | 630 |
| Gln | Ile | Gly | Val | Thr | Gly | Leu | Ser | Ala | Gly |
| | | | | 635 | | | | | 640 |
| Asp | Lys | Val | Tyr | Ile | Asp | Lys | Ile | Glu | Phe |
| Ile | Pro | Val | Asn. | | | | | | |

* * * * *

UNITED STATES PATENT AND TRADEMARK OFFICE
CERTIFICATE OF CORRECTION

PATENT NO. : 5,002,765

DATED : March 26, 1991

INVENTOR(S) : Herrnstadt et al

It is certified that error appears in the above-identified patent and that said Letters Patent is hereby corrected as shown below:

Column 3     line 23: "Norther" should read --Northern--.
Column 5     line 51: "trp gene, lac gene, gal gene" should read --trp gene, lac gene, gal gene--.
Column 7     line 20: "east" should read --ease--.
Column 10    line 24: "55 gm yeast estract" should read --5 gm yeast extract--.
                 line 26: "8 urea" should read --8 M urea--.
Column 12    line 20: "E. coli" should read --E. coli--.
                 line 32: "environmentally by" should read --environmentally stable by--.
Column 17    claim 3: "E. coli" should read --E. coli--.

Signed and Sealed this

Eighth Day of September, 1992

Attest:

DOUGLAS B. COMER

Attesting Officer        Acting Commissioner of Patents and Trademarks